United States Patent [19]
Palermo

[11] Patent Number: 5,562,718
[45] Date of Patent: Oct. 8, 1996

[54] ELECTRONIC NEUROMUSCULAR STIMULATION DEVICE

[76] Inventor: Francis X. Palermo, 616 Vineyard Pt., Guilford, Conn. 06437

[21] Appl. No.: 253,415

[22] Filed: Jun. 3, 1994

[51] Int. Cl.$^6$ .................................................. A61N 1/18
[52] U.S. Cl. ............................................. 607/46; 607/72
[58] Field of Search ................................ 607/46, 48, 61, 607/60, 66, 70, 72, 74, 75, 115, 2

[56] References Cited

U.S. PATENT DOCUMENTS

| | | | |
|---|---|---|---|
| 3,648,708 | 3/1972 | Haeri | 607/72 |
| 4,576,171 | 3/1986 | Key | 607/46 |
| 4,895,154 | 1/1990 | Bartelt et al. | 607/72 |
| 4,919,139 | 4/1990 | Brodard | 607/74 |
| 5,048,523 | 9/1991 | Yamasawa et al. | 607/72 |

*Primary Examiner*—William E. Kamm
*Assistant Examiner*—Scott M. Getzow
*Attorney, Agent, or Firm*—Albert O. Cota

[57] ABSTRACT

An electronic neuromuscular stimulation device (10) that is operated by a computerized electronic control unit (20). The unit (20) includes at least two and preferably four output channels to which are connected a corresponding set of electrode output cables (12). Each cable has attached a positive electrode (12D) and a negative electrode (12E) that are attached to selected areas of a patient's anatomy. The unit (20) also includes controls, indicators, and circuitry that produce nerve stimulation pulses that are applied to the patient through the electrodes (12D,12E). The nerve stimulation pulses consist of individual pulses that are arranged into pulse trains and pulse train patterns. The pulse train patterns, whose selection depends on the type of ailment being treated, includes sequential patterns, delayed overlapping patterns, triple-phase overlapping patterns, reciprocal pulse trains, and delayed sequenced "sprint interval" patterns. The overlapping patterns are particularly timed to take advantage of neurological enhancement.

19 Claims, 7 Drawing Sheets

OUTPUT PULSES, TRAINS AND TRAIN PATTERNS

INDIVIDUAL PULSES

MONOPHASIC SQUARE WAVE

- PULSE WIDTH: 40-50 MICROSECONDS
- VOLTAGE AMPLITUDE: 0-150 VOLTS

Fig. 4A.

BIPHASIC ASYMMETRIC SQUARE WAVE

- POSITIVE PHASE PULSE WIDTH: 40-50 MICROSECONDS
- VOLTAGE AMPLITUDE: 0-150 VOLTS

Fig. 4B.

PULSE TRAINS

MAIN OPERATING FREQUENCY

- PULSE INTERVALS: 10-20 MILLISECONDS (50-100 Hz)

Fig. 4C.

RAMP FREQUENCIES

- 18 - 50 Hz PROGRESSION OVER 0.5-2.0 SECONDS

Fig. 4D.

PULSE TRAIN PATTERNS

SEQUENTIAL

A AND C:   200 MILLISECONDS

B:   160 MILLISECONDS

Fig. 4E.

DELAYED OVERLAP

A:   200 MILLISECONDS

Fig. 4F.

TRIPLE PHASE OVERLAP

A AND G:   200 MILLISECONDS
B:   40 MILLISECONDS
C:   120 MILLISECONDS
D:   20 MILLISECONDS
E:   100 MILLISECONDS
F:   160 MILLISECONDS

Fig. 4E.

RECIPROCAL

A: RAMP

B: MAIN PULSE TRAIN

Fig.4H.

DELAYED SEQUENCED "SPRINT INTERVAL"

Fig.4I.

ELECTRONIC NEUROMUSCULAR STIMULATION DEVICE

TECHNICAL FIELD

The invention pertains to the general field of electronic nerve and muscle stimulators, and more particularly to an electronic neuromuscular stimulation device that produces short overlapping pulse train patterns that are timed to take advantage of neurologic enhancement.

BACKGROUND ART

The problems associated with diseases which affect the human central nervous system such as Parkinsons disease, multiple sclerosis, muscular dystrophy and strokes produce various ailments that include orthopedic or musculoskeltel pain such as patello-femoral pain and post-operative hip pain, muscle spasms, disuse muscle atrophy, post-operative venous thrombosis, spasticity, poor blood circulation, ataxia and various other acute and chronic pain. To treat these and other related medical ailments, there are two dominant electronic, nerve stimulation devices in use: a transacutaneous electrical nerve stimulation (TENS) device and a neuromuscular stimulation (NMS) device. The TENS devices are utilized to mask pain signals in a human body before the signals reach the brain, thus, giving a patient apparent relief from the pain.

The prior art NMS devices produce electrical d-c pulses that are applied to the skin of a patient by one or more electrodes. The electrodes are placed over the muscle to be stimulated in order to activate or contract the muscle. The timing characteristics of the applied pulses are usually predetermined by the prescribing doctor or they may be individually selected or controlled by switches available to be operated by the patient.

The pulses produced in the prior art are in the range of 100 to 300 microseconds and are applied as either a continuous pulse train as typically used in the TENS device; or as repetitive pulse trains that range between 1,000 to 15,000 milliseconds as typically used in the NMS devices. The TENS devices provide only transient benefits from pain. Thus, within minutes after stopping a TENS device, the effect is diminished. Also, the pulses used in the prior art NMS devices are at a relatively high intensity that produce powerful muscle contractions. In contrast, the device of the instant application does not cause powerful contractions but rather produces very brief twitches of the muscle and smaller movements of the joint. This application technique helps to decrease disuse atrophy, to improve a joint range of motion and to decrease pain for prolonged periods of time.

The instant application further differs from the prior art devices in that the individual pulses are in the range of 30 to 50 microseconds, are preset and are applied in some cases in partially overlapping pulse trains having overlaps that range between 20 to 50 milliseconds. The overlapping trains are specifically timed to take advantage of neurologic enhancement and/or inhibition either of which increase coordination and strength or decrease excessive muscle tone or spasms. The overlapped pulses are particularly intended to follow the naturally or physiologically occurring co-contraction of opposing muscle which produces joint stabilization as the limb rapidly changes direction. Also, the results achieved by the instant invention are either immediate or may not begin to take effect unit the day after multiple applications. Thus, long lasting pain relief of up to a few weeks has been achieved.

A search of the prior art did not disclose any patents that read directly on the claims of the instant invention, however the following U.S. Pat. Nos. are considered related:

| U.S. Pat. No. | INVENTOR | ISSUED | |
|---|---|---|---|
| 4,926,865 | Oman | 22 May | 1990 |
| 4,926,864 | Dufresne et al | 22 May | 1990 |
| 4,622,973 | Agarwala | 18 November | 1986 |
| 4,392,496 | Stanton | 12 July | 1983 |
| 4,340,063 | Maurer | 20 July | 1982 |

The U.S. Pat. No. 4,926,865 Oman patent discloses a microcomputer-based transcutaneous electrical nerve stimulation (TENS) device that controls pulse duration, pulse repetition rate, stimulation duty cycle, and modulation of pulse parameters. The device may be used either for pain relief or to facilitate muscle contractions. The intensity of the stimulation is determined by the amplitude and duration of the individual pulses, while the pulse rate determines the perceived continuity of the applied stimulation.

The U.S. Pat. No. 4,926,864 Dufresne et al patent discloses a microcomputer-based transacutaneous electrical nerve stimulation (TENS) device. The device operates from a 3-volt battery that is applied to a step-up voltage circuit to create a high-voltage level energy source that is applied to a patients skin. The step-up voltage circuit stores and subsequently supplies a plurality of amplitude timing signals to an output circuit from where the timed signals are applied to a patient's skin to mask pain signals before they reach the brain.

The U.S. Pat. No. 4,622,973 Agarwala patent discloses a neuromuscular stimulation (NMS) device that causes muscle to contract by applying to a patient's skin a plurality of programmable electrical pulses. The device is typically used therapeutically when there is a lack of neuro-motor faculty, or when muscles have become weakened or damaged by disease or trauma.

The U.S. Pat. No. 4,392,496 Stanton patent discloses a neuromuscular stimulator device which provides external electrical stimulus induced muscle exercise to retard or prevent tissue atrophy. The device provides, on two output channels, alternating pulses through electrodes that connect to a patient's skin. The applied pulses are increased in intensity at a variable rate until a prescribed fixed intensity is reached. The pulses are also applied during an adjustable predetermined stimulation interval and removed during a resting interval which occurs alternately. The amplitude limit of the pulse is adjustable by a patient within an upper limit established by a clinician at the time the device is set up for the patient.

The U.S. Pat. No. 4,340,63 Maurer patent disclose a stimulation device that electrically stimulates living tissue, including body organs, muscles and nerves. The device produces a series of pulses that are applied to the surface of the body or invasively implanted in the body. The device includes an electrical circuit that includes a control for varying the pulse width, stimulus intensity, pulse repetition rate, and the on-time of the pulse to vary the pulse width. The pulse width variation is dependent upon the optimal pulse width desired for a particular nerve tract or bundle. The applicant's device does not vary the pulse width or the pulse repetition rate.

for background purposes and as indicative of the art to which the invention relates reference may be made to the patent issued to:

| U.S. Pat. No. | INVENTOR | ISSUED | |
|---|---|---|---|
| 5,133,354 | Kallok | 28 July | 1992 |
| 5,097,833 | Campos | 24 March | 1992 |
| 5,070,873 | Graupe et al | 10 December | 1991 |
| 4,976,264 | Petrofsky | 11 December | 1990 |
| 4,832,033 | Maher et al | 23 May | 1989 |
| 4,642,769 | Petrofsky | 10 February | 1987 |
| 4,480,830 | Petrofsky et al | 6 November | 1984 |
| 4,324,253 | Greene et al | 13 April | 1982 |
| 4,147,171 | Greene et al | 3 April | 1979 |
| 4,817,254 | Maurer | 18 June | 1974 |

DISCLOSURE OF THE INVENTION

The neurological stimulation device is designed to apply to selected area of living tissue, in both human and animals bodies, a series of electrical nerve stimulation pulses which take the form of sequential, or dual and triple overlapping pulse train patterns. The application of the train patterns produces very brief twitches of the muscle and small movements of the joint to help decrease disuse atrophy; improve a joint range of motion; and to decrease pain for prolonged time periods which in some cases, extends into days. In addition, movement coordination is somewhat restored.

In its basic form, the electronic neuromuscular stimulation device consists of a plurality of electrode output cable having a front section and a back section. The front section is split and has attached a pair of electrodes such as transcutaneous electrode pads that are adapted to be attached to the selectable areas of the living tissue. The back end has a male jack that is inserted into one or as many as six output channels located on an electronic control unit that operates the device.

The electronic control unit in its basic form is comprised of:

a) a power input circuit that consists of a battery charger having an input that is applied an a–c power source and an output that is applied to a charge/run switch having a CHARGE contact and a RUN contact. When the switch is placed in the CHARGE position, a rechargeable battery is maintained in a charged condition, b) a power application circuit consisting of a latching relay, a POWER ON switch, a POWER ON indicating lamp and a power regulator. When the charge/run switch is placed in the RUN position and the POWER ON switch is pressed, the relay is energized. When the relay is energized, the power from the battery is applied to the voltage regulator and the POWER ON indicating lamp illuminates, c) a power control circuit consisting of a power control unit that is energized by a low voltage detector when the battery voltage drops to an unacceptable operating level. The power unit is also energized by a treatment concluded output signal that is applied when a patient's treatment has been concluded. In either instance, when the power unit is energized, it de-energizes the latching relay, to terminate the power to the neurological stimulation device, d) a PULSE PATTERN SELECT switch that selects an output signal corresponding to a specific pulse output pattern, e) a pulse-pattern generating circuit consisting of a microprocessor that functions in combination with a programmable read only memory (PROM) and a firmware program. The pulse-pattern generator circuit is energized by the voltage regulator, and is applied the input from the PULSE-PATTERN SELECT switch. The output of the pulse-pattern generating circuit consists of a plurality of pulse signals, and the treatment concluded output signal, f) a pulse driving circuit consisting of a plurality of FET drivers that are applied the respective output signal from the pulse-pattern generating circuit. The FET drivers produce a corresponding set of first and second output signals, and g) a pulse output circuit consisting of a plurality of isolation and impedance matching transformers and a plurality of PULSE SET switch/potentiometer units. The output signals from the pulse driving circuit are applied to a respective transformer and to the pole of the switch. When the potentiometer is adjusted so that the switch is closed, the selected nerve stimulation pulse is routed through the potentiometer wiper and said coupling capacitor to a paired-dipole PULSE OUTPUT connector. To this connector is attached the output cable that is attached to the living tissue.

The method for applying the nerve stimulation pulses to the living tissue is comprised of the following steps:

a) attaching the electrode pads of the electrode cables to the selected areas of the living tissue, b) selecting by means of the PULSE PATTERN select switch the particular pulse train pattern that is to be applied to the living tissue through said electrode cable, c) setting the PULSE SET switch/potentiometers to OFF, d) pressing the START SWITCH, and e) progressively adjusting the PULSE SET switch/potentiometers to apply a pulse train that produces a non-painful, gentle muscle contraction through cyclical activation of the motor nerves branching into the muscles under or near the electrode pads.

The timing of the sequential, dual and triple overlapping pulse train patterns is precise to take advantage of the human or animal central nervous system inhibition and facilitation. The repetitive cycling of the pulse trains is fast and closely emulates adult reciprocating limb speeds from slow gentle leg or arm movements to the fastest running patterns.

The type of patients that can be helped by the repeated application of the neurological stimulation device are those patients with: motor memory or coordination deficits, weakness, spasticity and dystonia tremor and ataxia, joint pain and stiffness, muscle pain and pain due to sympathetic or vascular origins.

In general, the electrode placement is as follows: note that channel 1 is applied to Agonist and channel 2 to Antagonist. When more than two channels are used, it requires practitioner determination of desired muscle group interactions:

| | AGONIST | ANTAGONIST |
|---|---|---|
| ⓛ Upper Extremities Use Overlapping Pattern | Biceps Finger Flexors including hand intrinsics | Triceps Finger Extensors |

Cycle Speed(Cs): Slow (0.66 Hz) or fast (1.5 HZ) or triple phase

ⓛ Neck: Use Upper Extremity Overlap Pattern
CS: slow or fast    Left and Right Cervical Paraspinal Muscles ⓛ Back: Use Lower Extremity Overlap Pattern
CS: slow    Left and Right Lumbar paraspinal Muscles -continued

|  | AGONIST | ANTAGONIST |
|---|---|---|
| ⓓ Unilateral -Lower Extremities: CS: slow overlap or triple phase | Hip-anterior lateral hip and quadriceps Knee-Quadricep Ankle-Anterior Tibialis | posterior hip and hamstrings Hamstring Gastroc/ Soleus |
| ⓓ Bilateral -Lower Extremities: | Left and Right Quadriceps May be used with left and right hamstrings with a four channel system and with left and right lumbar paraspinals with a six channel system | |

CS: slow, fast, very fast (2.2 Hz), fastest (3.3 Hz). Simulating a slow walk, fast walk, running and sprinting respectively.

These and other objects and advantages of the present invention will become apparent from the subsequent detailed description of the preferred embodiment and the appended claims taken in conjunction with the accompanying drawings.

BEST MODE FOR CARRYING OUT THE INVENTION

The best mode for carrying out the invention is presented in terms of a preferred embodiment that creates coordination enhancement by stimulation of the nerves and/or muscles by applying electronically derived nerve stimulation pulses.

The preferred embodiment of the electronic neuromuscular stimulation device 10, as shown in FIGS. 1–4, is comprised of three major elements: at least one electrode output cable 12, a utility power cable 14 and an electronic control unit 20.

Figure 1:
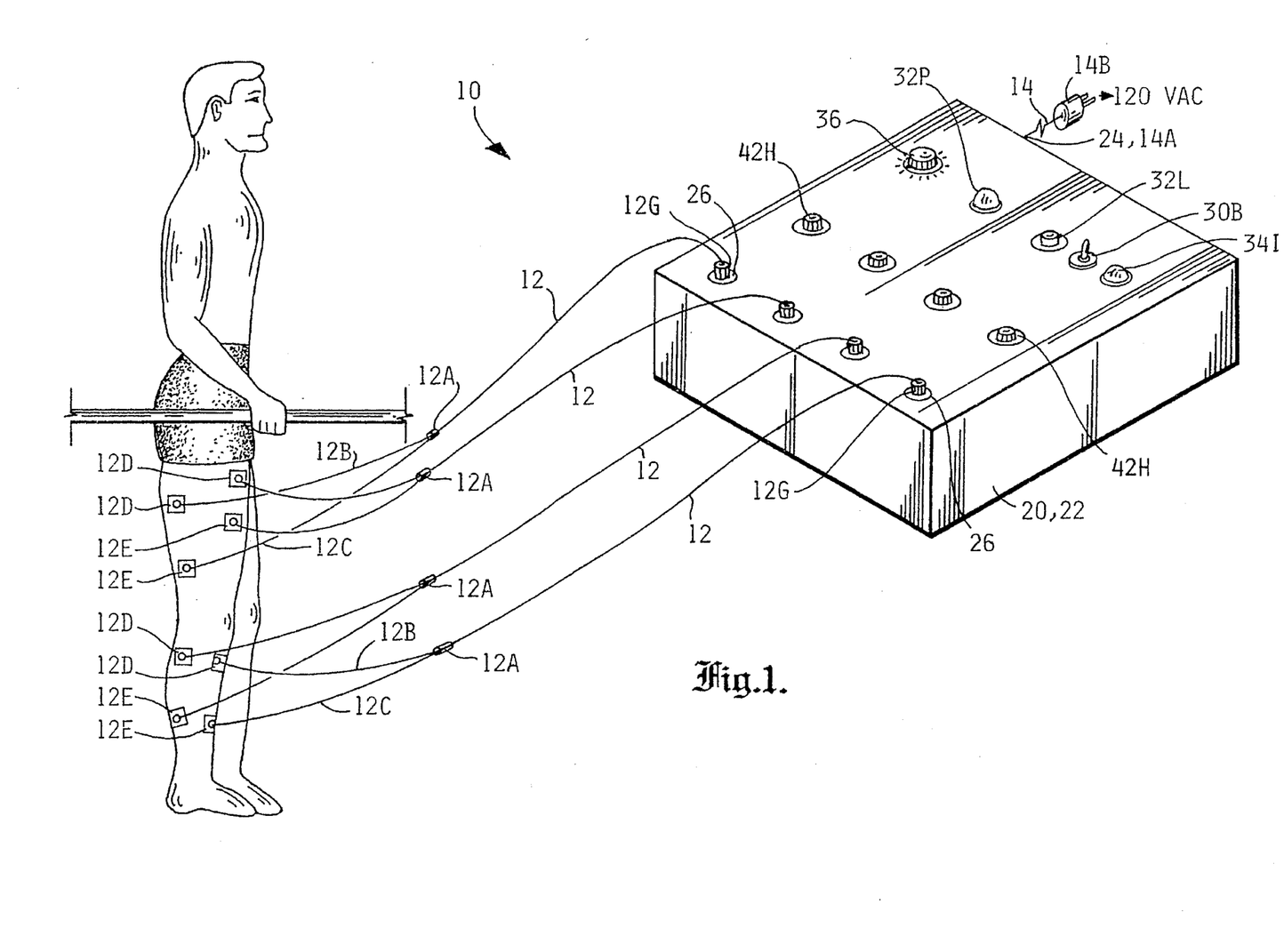
FIG. 1 is a perspective view of the electronic neuromuscular stimulation device showing the various operating controls and the device connected to a human body by means of a plurality of electrode output cables.
Figure 2A:
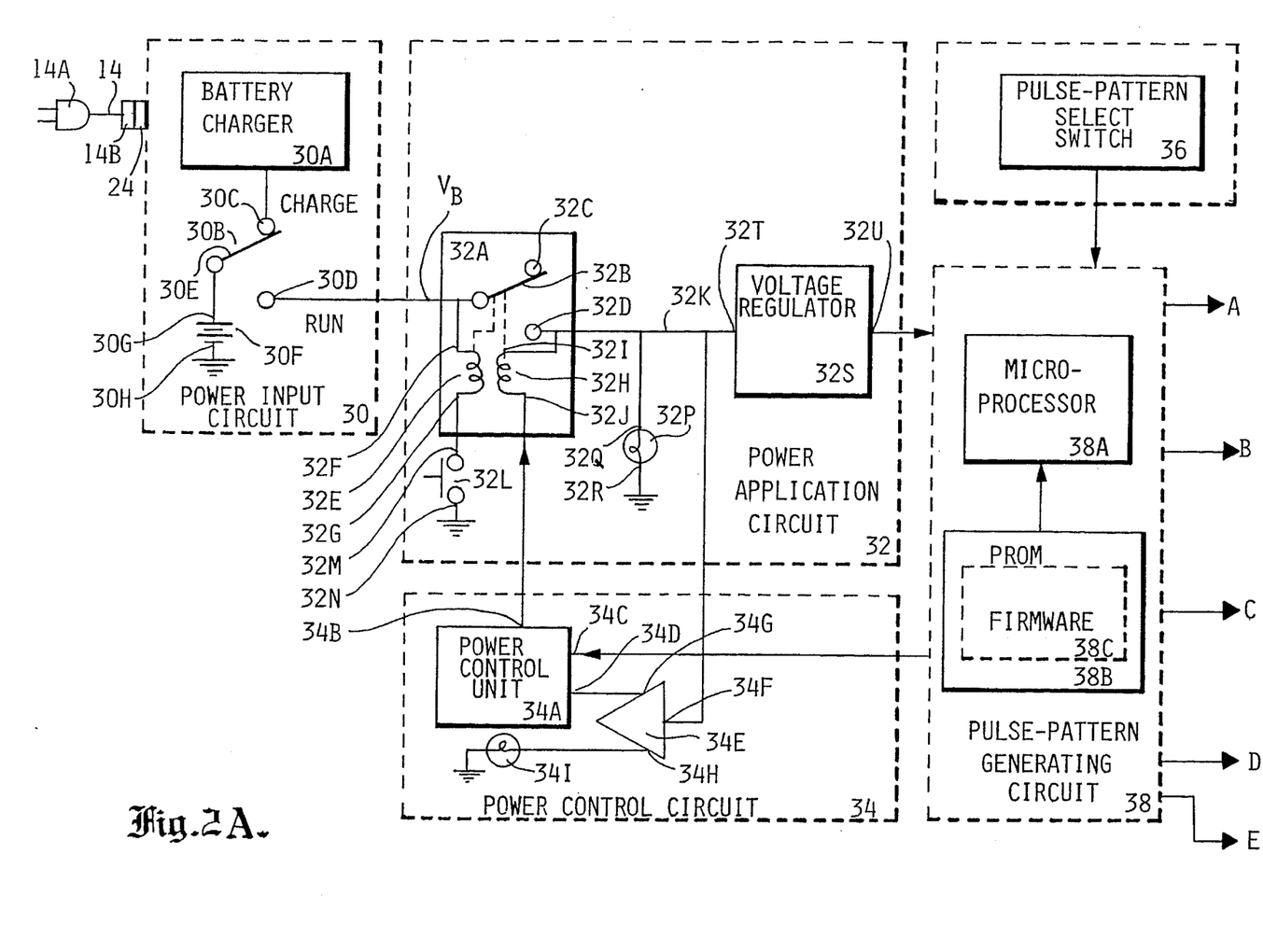
FIGS. 2A and 2B is a combination schematic/block diagram of the electronic control unit and the connection to the unit of the utility power cable and the electrode output cables.
Figure 2B:
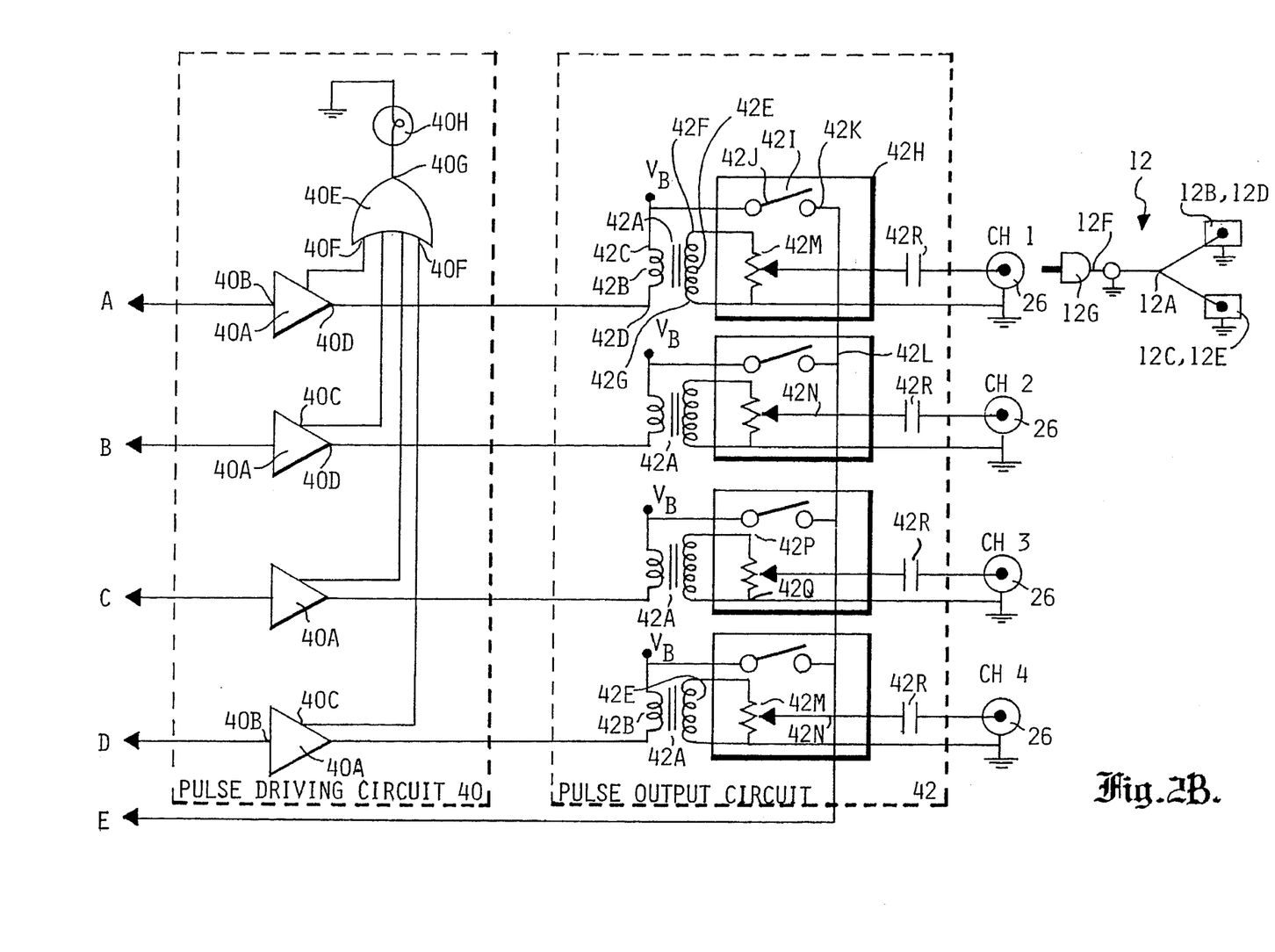

The electrode output cable 12 as shown in FIGS. 1 and 2, has a front section 12A that splits into a first split end 12B and a second split end 12C; and a back section 12F that has attached a male jack 12G. The cable can be manufactured out of two separate leads. However, a coaxial cable is preferably used that has attached to its back section 12F, a coaxial male jack 12G. To the first split end 12B is attached a positive electrode 12D and to the second split end 12C, a negative electrode 12E. Preferably, the electrodes consist of transcutaneous electrode pads. However, a needle electrode, or a combination of electrodes that use a transcutaneous electrode on one of the split ends and a needle electrode on the other split end may also be used.

The electronic control unit 20 as shown physically in FIG. 1 and in a combination schematic/block diagram in FIGS. 2A and 2B is comprised of the following major elements: a portable enclosure 22, an upper panel 23, a power input circuit 30, a power application circuit 32, a power control circuit 34, a PULSE PATTERN select switch 36, a pulse generating circuit 38, a pulse driving circuit 40 and a pulse output circuit 42.

The primary power to the device 10 is provided through a male power-input receptacle 24 located on the enclosure. Into the receptacle is attached the female connector 14A of a utility power cable 14. The other end of the cable 14 has a male plug that plugs into a 120-volt a–c utility power receptacle.

The enclosure 22 also has an upper panel 23 as shown in FIG. 1, which has mounted all the operating controls for the device 10 which include a set of PULSE OUTPUT connectors 26, where the set may consist of at least two connectors 26 but preferably with either four connectors 26 or six connectors 26; a set of either four or six PULSE SET switch/potentiometer units 42H; the PULSE PATTERN select switch 36; the START switch 32L; the CHARGE/ RUN switch 30b, the POWER ON indicator lamp 32P and the LOW BATTERY indicating lamp 34I. The panel 23 is preferably designed with cut-outs to which are attached the switches, controls and lamps. Alternatively, a panel having membrane and/or capacitive switches, controls and internal lamps may also be used to preclude the ingress of fluids into the electronic elements located within the enclosure 22 of the electronic control unit 20.

The plurality of PULSE OUTPUT connectors 26 externally interface with a respective male jack 12G on one of the electrode output cables 12. The electronic control unit 20 also has circuit means for selectively producing a plurality of nerve stimulation pulse train patterns. These patterns, are applied to the patient through the male jacks 12G and the electrode pads 12D,12E on the electrode output cables 12.

The power input circuit 30 as shown in FIG. 2A is applied 120-volts a–c when the female connector on the utility power cable 14 is inserted into the male power-input receptacle 24 on the enclosure. The a–c power input is conditioned by and applied through a battery charger 30A that is connected to a CHARGE contact 30C of a single-pole double-throw charge/run switch 30B which also has a RUN contact 30D and a pole 30E. The pole 30E is connected to the positive terminal 30G of a rechargeable battery 30F that has its negative terminal 30H connected to circuit ground. The battery may consist of either a nickel cadmium battery, a gel cell or the like.

The power application circuit 32 as shown in FIG. 2A, is comprised of a latching relay 32A, a push-button START switch 32L, a POWER-ON indicator lamp 32P and a voltage regulator 32S. The latching relay 32A has a pole 32B, a normally-open first contact 32C, a second contact 32D, a first coil 32E having a first end 32F and a second end 32G, and a second coil 32H having a first end 32I and a second end 32J. The relay pole 32B and the first end 32F of the first coil 32E are connected to the RUN contact 30D of the charge/run switch 30. The first end 32I of the second coil 32H is connected to a first junction 32K to which is also connected the second contact 32D of the relay 30.

The normally open push-button START switch 32L has a first contact 32M that is connected to the second end 32G of the first coil and a second contact 32N connected to circuit ground. The POWER-ON indicator lamp 32P has a first terminal 32Q that is connected to the first junction 32K and a second terminal 32R connected to circuit ground. The voltage regulator 32S has an input terminal 32T connected to the first junction 32K and an output terminal 32U.

The power control/circuit 34 is comprised of a power control unit 34A, a low-voltage detector 34E and a LOW-BATTERY indicating lamp 34I. The power control unit 34A has an output terminal 34B, a first input terminal 34C and a second input terminal 34D. The output terminal 34B is connected to the second end 32J of the second coil 32H. The low-voltage detector 34E has an input terminal 34f that is connected to the first junction 32K, a first output terminal 34G that is connected to the first input terminal of the power control unit 34A and a second output terminal 34H that is connected to the low-voltage indicating lamp 34I.

The PULSE PATTERN SELECT switch 36, as also shown in FIG. 2A, may consist of a conventional rotary switch or a binary encoded switch. In either case, the switch has means for providing logic level signals that function to select a plurality of output pulse trains and train patterns as described infra.

The pulse pattern generating circuit includes a microprocessor 38A that functions in combination with a programmable read only memory (PROM) 38B and a firmware program 38C. In lieu of a PROM 38B, a replaceable eraseable programmable read only memory (EPROM) may be used. The use of an EPROM allows the firmware program 38C to be altered or changed to accommodate the parameters of a specific nerve stimulation pulse(s). The PROM or EPROM provide the following nerve stimulation pulse parameters; pulse width, pulse train duration, pulse train delay/overlap, pulse train ramp (ramp frequency), pulse train repetition cycling, and pulse train on-time. The pulse pattern generating circuit 38 has a first input supplied from the output terminal 32U of the voltage regulator 32S that energizes the circuit 38. A second input is supplied from the PULSE-PATTERN SELECT switch 36. The switch allows the specific pulse train and train pattern that is to be processed by the pulse pattern generating circuit 36 to be selected. The output of the circuit 38 consists of a plurality of pulse outputs that preferably are comprised of either four or six outputs and a treatment concluded output signal that is automatically applied to the power control unit 34A. The output signal turns the electronic neuromuscular stimulation device 10 off when a patient's treatment has been concluded.

The pulse driving circuit 40 as shown in FIG. 2B consists of a plurality of FET drivers 40a and an ORing circuit 40E. The FET drivers 40A have input terminals 40B that are applied the respective output signals from the pulse-pattern generating circuit 38. Each of the FET drivers have a first output terminal 40C and a second output terminal 40D.

The ORing circuit may consist of either a discreet grouping of diodes arranged in an "OR" configuration or an integrated OR gate 40e as shown in FIG. 2B. The OR gate 40E has a plurality of input terminals 40F that are applied the first inputs 40C from the FET drivers 40A. The ORing circuit has an output terminal 40G that is connected to a STIMULUS ON indicating lamp 40H.

The pulse output circuit 42 consists of a plurality of isolation and impedance matching transformers 42A and a plurality of PULSE SET switch/potentiometer units 42H. Each transformer 42A has a primary winding 42B having a first terminal 42C and a second terminal 42D, and an isolated secondary winding 42E having a first terminal 42F and a second terminal 46G.

The PULSE SET switch/potentiometer units 42H each consist of a single-pole single-throw switch 42I and a potentiometer 42M. Each switch 42I has a pole 42J and a contact 42K. The contact 42K of each switch 42I is connected to a second junction 42L to which is also connected the third input of the microprocessor 38A which is applied to the pulse-pattern generating circuit 38. Each potentiometer 42M has a wiper 42N, a first terminal 42P and a second terminal 42Q. The first terminal 42C of the transformer's primary winding 42B is connected to the battery voltage $V_B$ and to the pole 42J of each switch 42I. The second terminal 42D of the primary winding 42B is connected to the output of a respective FET driver 40A. The first terminal 42F and second terminal 42G of the secondary winding 42E is connected respectively across the first terminal 42P and second terminal 42Q of the potentiometer 42M. The wiper 42N of each potentiometer 42M is capacitively coupled through a capacitor 42R to a positive contact of a respective pulse output connector 26 on said enclosure 22. The second terminal 42Q is connected to the negative side or circuit ground side of the pulse output connector.

The electronic control circuit operates the electronic neuromuscular device 10 as follows: the input power into said electronic control unit is applied from the utility power cable 14 through the battery charger 30A to said charge/run switch 30B. When the charge/run switch is placed in the CHARGE position 30C, the recargeable battery 30F is charged through the pole 30B of the switch 30E. When the switch 30b is placed in the RUN position 30D, the battery voltage $V_B$ as shown in FIG. 2A, is applied to the pole 32B of the latching relay 32A which is normally in contact with the normally open contact 32C of the relay. When the normally-open push-button START switch 32L is depressed, the battery voltage $V_B$ energizes the relay 32A causing the relay pole 32B to make contact with the second contact 32D of the relay 32A. At this occurrence, the battery voltage $V_B$ is applied to a first junction 32K to which is also connected the input terminal 32T of the 5-volt voltage regulator 32S and the power-on indicator lamp 32P.

The power-on mode of the relay 32A is controlled by the relay's second coil 32H which is connected to the output terminal 34B of the power control unit 34A. When the low voltage detector 34E senses that the voltage level of the battery 30F has dropped to a level of 8.5 volts, the detector 34E energizes the LOW-BATTERY indicating lamp 34I through output terminal 34H. When the battery voltage drops to an unacceptable level of 7.5 volts, the detector through output terminal 34G energizes the power control unit 34A which then de-energizes the relay and turns the device 10 off. The power control unit 34A is also energized by the treatment concluded output signal that is applied by the pulse-pattern generating circuit 38 when a patient's treatment has been concluded.

The power output from the voltage regulator 32S is applied to the pulse-pattern generating circuit 38 where the microprocessor 38A in combination with the PROM 38b and the firmware 38C produces a plurality of output signals as selected by the PULSE-PATTERN select switch 36. The output signals from said pulse-pattern generating circuit 38 are each applied through the respective FET driver 40A which each have an output that is connected to the respective primary winding 42B of the isolation and impedance matching transformer 42A, and to the ORing circuit 40E.

When the ORing circuit is enabled, it causes the PULSE-OUTPUT indicating lamp 40H to illuminate. The output 40D of the FET driver 40A is also applied through the primary winding 42b of the transformer 42A to the pole 42J of the switch 42I on said pulse-set switch/potentiometer unit 42M. The secondary winding 42E of the transformer is connected across the respective resistive element of the potentiometer 42M of the PULSE-SET switch/potentiometer unit 42H. When the potentiometer 42M is adjusted so that the switch 42I is closed, the parameters of the selected pulse output can be adjusted and routed through the potentiometer wiper 42N and the coupling capacitor 42R to the PULSE output connector 26. To the connector, is then attached the electrode output cable 12 from where the nerve stimulation pulse is applied to the patient via the electrode output cable 12.

The device 10 can be designed to incorporate either two, four or six paired-dipole pulse output connectors (output channels)—for illustrative purposes, only four output channels are shown in FIGS. 1 and 2. If the device 10 incorporates four output channels 1 through 4, channels 1 and 3 are timed together, and channels 2 and 4 are timed together. When six output channels 1 through 6 are incorporated, channels 1, 3 and 5 are timed together and channels 2, 4 and 6 are timed together.

Figure 3:
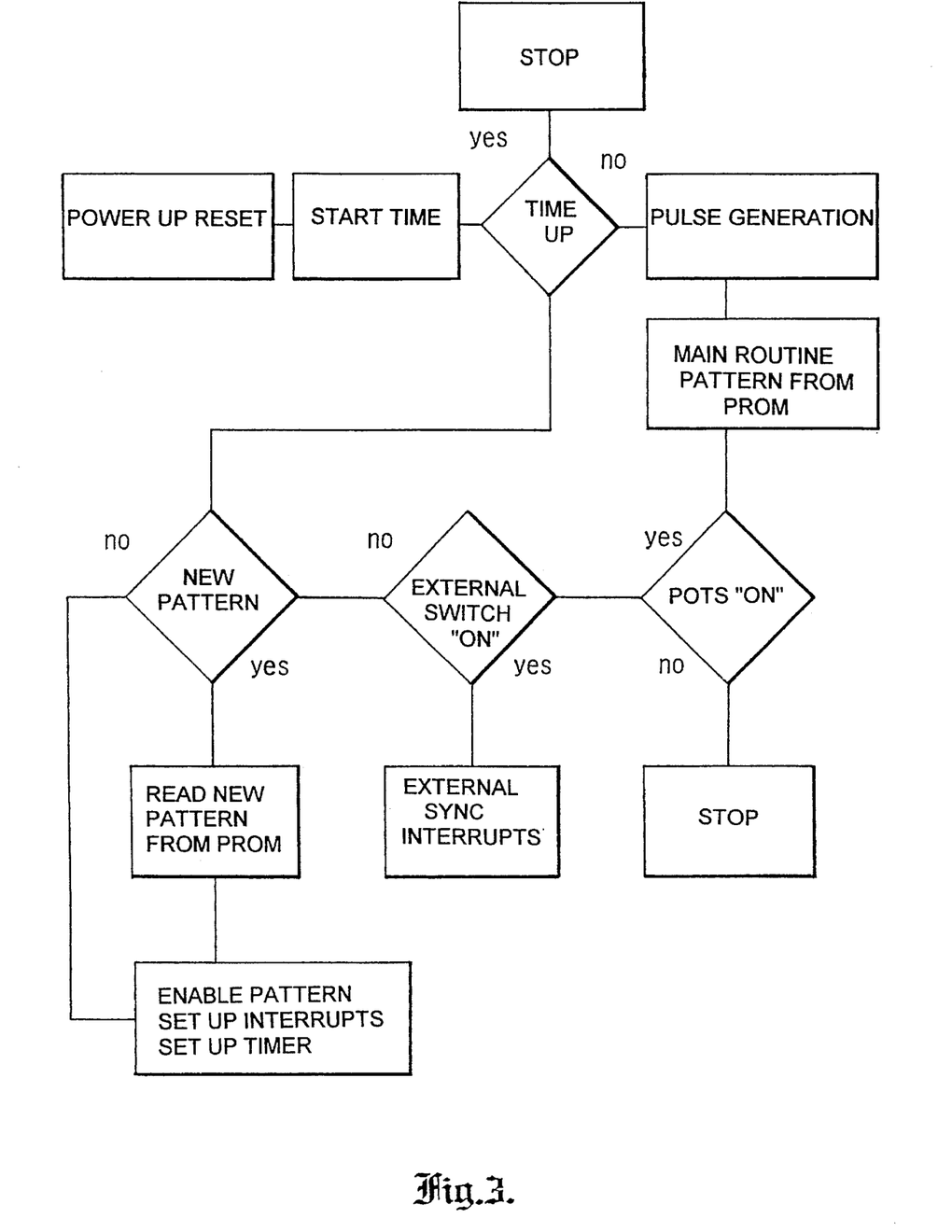
FIG. 3 is a flow diagram of the firmware program.

The firmware program 38C that operates the microprocessor 38A is shown in the flow diagram of FIG. 3. Explanatory statements corresponding to the flow blocks follows:

POWER UP RESET

Resets all timers to zero; interrupt external sync; Interrupt pulse output; set all output bits OFF; initializes input/output ports.

START-TIMER

Commences after the START switch 32L is pressed, and the PULSE SET switch/potentiometer 42H is turned ON.

PULSE GENERATION

Generates a pulse HIGH and a pulse LOW (HI:LO-OFF-TIME); indicates to main routine that a NEW PATTERN is required; retrieves new pattern and outputs new pulse pattern.

EXTERNAL SYNC INTERRUPTS

Interrupts routine from external sync input 0; and from external sync 1; turns pulse timers ON and disables sync interrupts and jumps to PULSE which generates a pulse.

STIMULATOR MAIN LOOP

1. Start up routine—initializes selected pattern, ensures that all PULSE SET switch/potentiometers 42H are OFF before starting; if any potentiometer is ON, the MAIN LOOP will stop running.

2. Main routine—waits for potentiometers 42H to be turned ON before enabling stimulator and starting 20-minutes timer; checks if any potentiometers remain ON; if any potentiometer is ON, main loop will continue running. If all potentiometers are OFF, after the routine begins, the MAIN LOOP will stop.

3. Retrieves pattern and variables for first section of pattern, and lookup next section of pattern. Pattern is ready from PROM and is determined by position of PULSE-PATTERN SELECT switch 36.

4. Enable pulse pattern to run and sets up interrupts and timer.

5. Run "infinite loop" that repeats pulse pattern selected until timer indicates that pulse pattern has timed out.

6. Subroutine to read PULSE-PATTERN SELECT switch and store the value and then set up pulse pattern lookup address.

The nerve stimulation pulses that are utilized in the device 10 are comprised of individual pulses, that are arranged into pulse trains and pulse train patterns. The particular nerve stimulation pulse used depends upon the particular ailment that is to be treated.

INDIVIDUAL PULSES

Figure 4A:
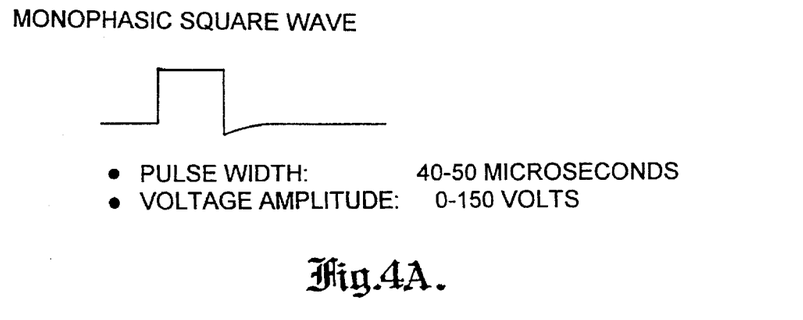
FIGS. 4A through 4I illustrate the various pulses, pulse trains and pulse train patterns that are available from the device for application to a patient.
Figure 4B:
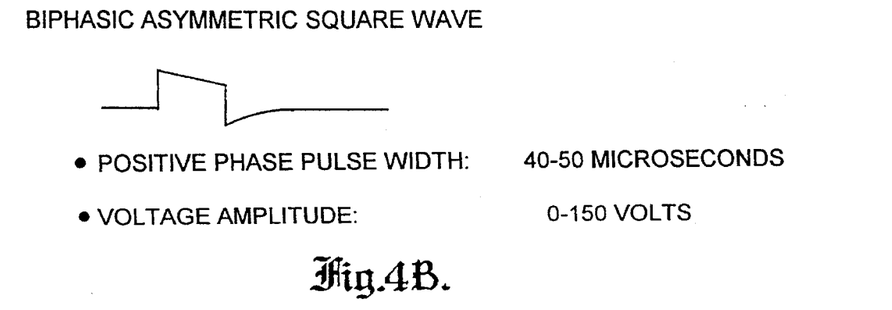

The individual pulses consist of either a monophasic square wave or a biphasic asymmetric square wave as shown in FIGS. 4A and 4B respectively. The monophasic square wave has an amplitude that ranges between 0 and 150 volts and a pulse duration that ranges between 40 and 50 microseconds; the biphasic asymmetric square wave as shown in FIGS. 4B also has an amplitude that ranges between 0 and 150 volts and a positive-phase pulse duration that ranges between 40and 50 microseconds.

PULSE TRAINS

Figure 4C:
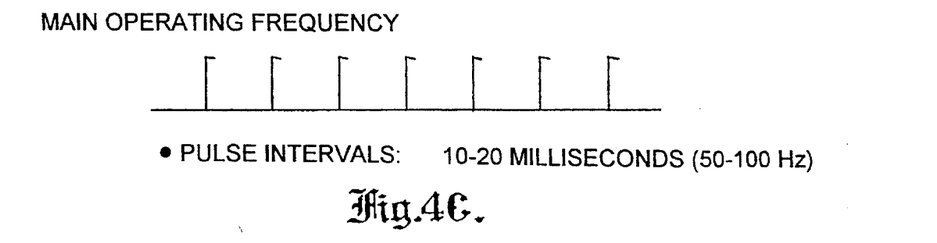
Figure 4D:
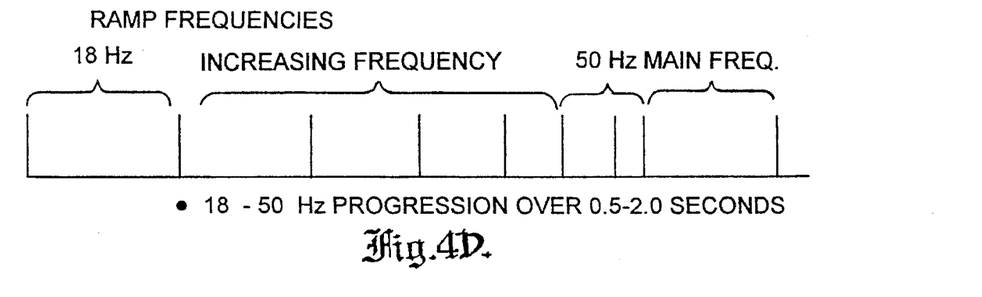

The pulse trains as shown in FIG. 4C operate at a pulse rate interval of between 10 and 20 milliseconds which corresponds to a frequency of between 50 Hz and 100 Hz respectively. If a ramp frequency is used, as shown in FIG. 4D, it is applied just prior to the application of a long pulse train. The ramp frequency varies between 18 and 50 Hz and progresses over a 0.5 to 2.0 second period.

PULSE TRAIN PATTERNS

Figure 4E:
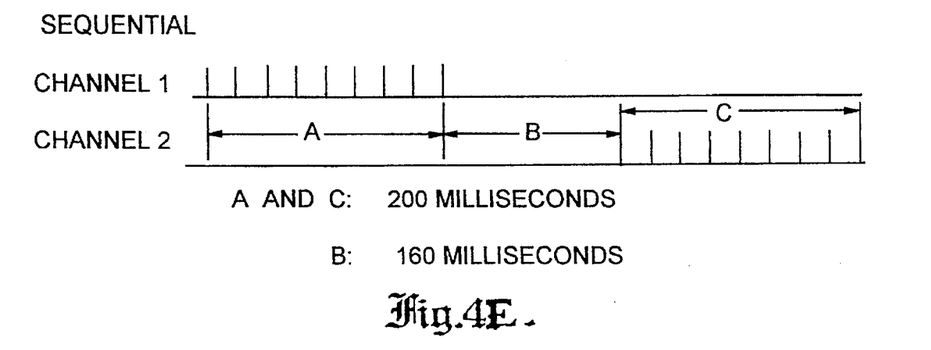

Sequential pulse train pattern—In the sequential pulse train pattern, output channels 1 and 2 are used to produce two pulse train patterns in which the second train commences after the first train has ended. As shown in FIG. 4E, a typical sequential pulse train pattern has a first pulse train pattern on channel 1 that lasts for 200 milliseconds. At the conclusion of the first pulse train pattern there is a time delay of between 60–200 milliseconds, or as illustrated a 160 millisecond time delay, before the second pulse train pattern of 200 milliseconds commences on channel 2.

Figure 4F:
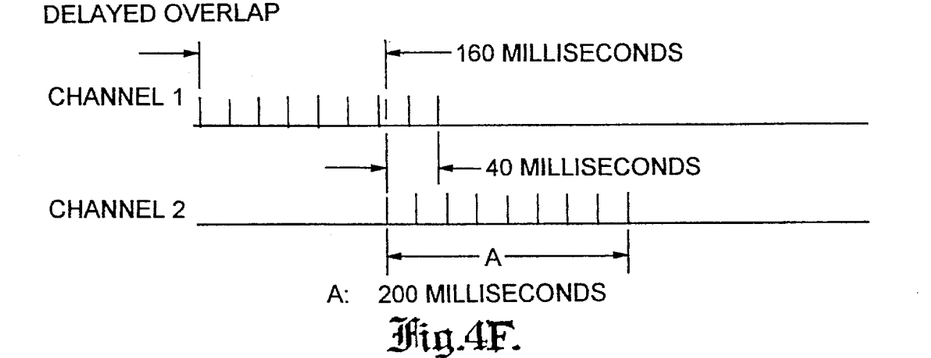

Delayed overlapping pulse-train pattern—In the delayed overlapping pulse-train pattern, output channels 1 and 2 are also used to produce two pulse train patterns: a first pulse train pattern on channel 1 and a second pulse train pattern on channel 2. The second pulse train pattern commences on channel 2 at a specified time period prior to the termination of the first pulse train pattern on channel 1. As shown in FIG. 4F, a typical delayed overlap pulse train pattern has a first pulse train pattern on channel 1 that lasts for 200 milliseconds. When this pulse train pattern has reached a time period of between 140 and 190 milliseconds or as illustrated a 160 millisecond time period, the second pulse train pattern of 200 millisecond commences on channel 2. Thus, as illustrated in FIG. 4F, there is an overlap of 40 milliseconds when channel 1 and channel 2 are each providing a composite pulse train pattern stimulation to a patient.

Figure 4G:
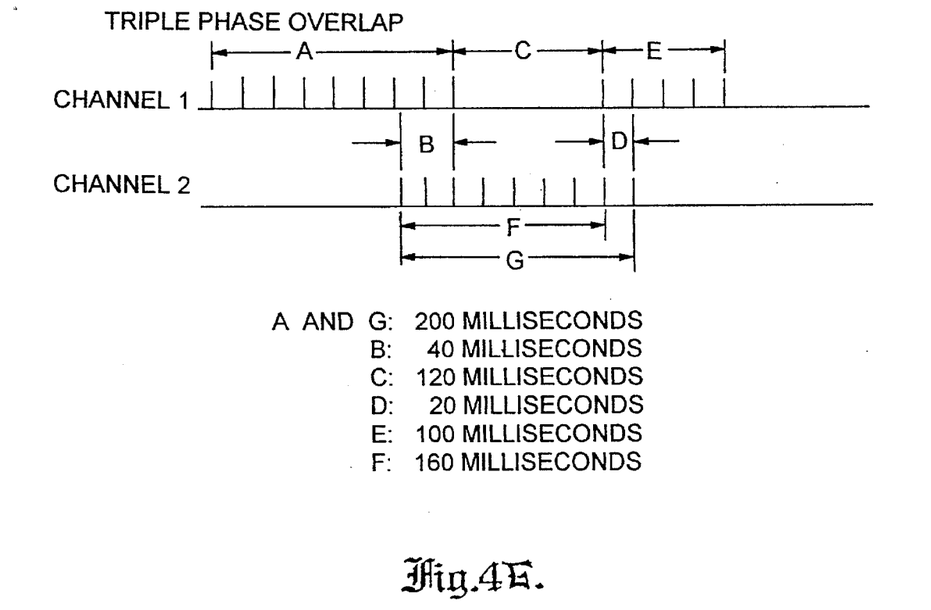

Triple-phase overlapping pulse-train pattern—In the triple phase overlapping pulse train pattern, channels 1 and 2 are used to produce three pulse train patterns: a first pulse train pattern on channel 1, a second pulse train pattern on channel 2 and a third pulse train pattern on channel 1. In this application, the second pulse train pattern commences on channel 2 at a specified time period prior to the termination of the first pulse train pattern on channel 1; then after a specified time period and prior to the termination of the second pulse train pattern on channel 2, the third pulse train pattern, which has a shorter time duration than that of the first pulse train pattern commences on channel 1. As shown in FIG. 4G, a typical triple phase overlap that is used to treat lower extremity problems, would have a first pulse train pattern on channel 1 that lasts for 200 milliseconds. When this first pulse train pattern has reached a timer period of between 150 and 170 milliseconds or as illustrated a time period of 160 milliseconds, the second pulse train pattern of 200 milliseconds commences on channel 2 which provides a first overlap of 40 milliseconds. When the second pulse train pattern has reached a time period of between 170 and 190 milliseconds or as illustrated a time period of 180 milliseconds, the third pulse train pattern which as a 100 millisecond time period commences on channel 1 prior to the termination of the second pulse train pattern to provide a second overlap of 20 milliseconds and a time lapse of 120 milliseconds between the termination of the first pulse train pattern and the beginning of the third pulse train pattern. The cycle repeats itself every 1.5 second (0.66 Hz) or every 0.75 seconds (1.5 Hz). Thus, as illustrated in FIG. 4G, channels 1 and 2 in addition to providing single pulse stimulation also provide a dual composite pulse train pattern stimulation at the termination of the first pulse train pattern and at the beginning of the third pulse train pattern. For upper extremity applications, the train and delay times are halved.

Figure 4H:
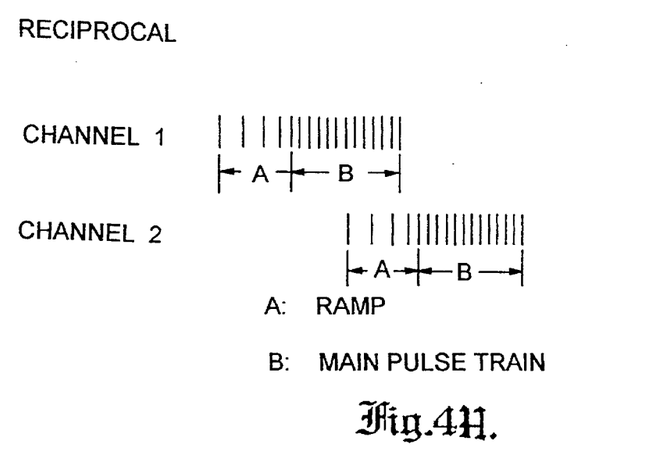

Reciprocal pulse train—In this pulse train pattern, a second pulse train pattern on channel 2 commences before the termination of a first pulse train pattern on channel 1. The second pulse train pattern commences, with an overlapping ramp that begins at a low voltage amplitude and ramps up to the maximum voltage amplitude that is available at the termination of the first pulse train pattern. A typical reciprocal pulse train pattern is shown in FIG. 4H.

Figure 4I:
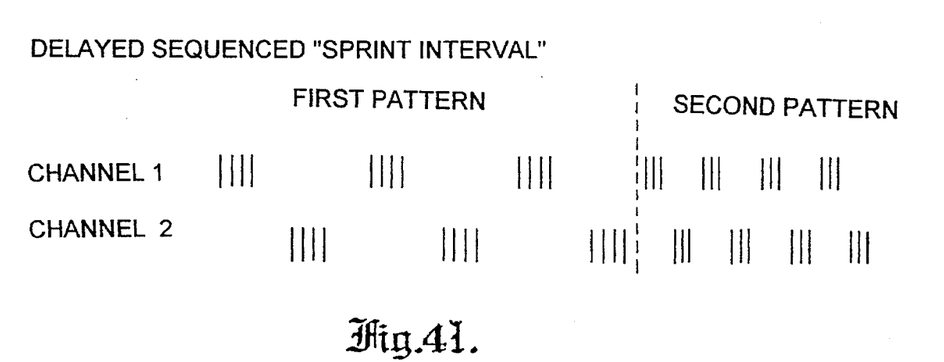

Delayed sequenced "spring interval" pulse train—In this pulse train pattern design, sequential pulse train patterns switch from one pulse train rate (cycling speed) and pulse train duration to another pulse train pattern having a different pulse train rate and pulse train duration. For example, as shown in FIG. 4I, on channel 1 there would occur three segments of a first pulse train pattern where each segment is separated by a specified time period. Following this pulse train pattern, also on channel 1, there would occur four segments of a pulse train pattern having a different train rate. Concurrently with the pulse train pattern on channel 1, there is on channel 2, similar but staggered pulse trains patterns.

While the invention has been described in complete detail and pictorially shown in the accompanying drawings it is not to be limited to such details, since many changes and modifications may be made in the invention without departing from the spirit and scope thereof. Hence, it is described to cover any and all modifications and forms which may come within the language and scope of the appended claims.

I claim:

1. An electronic neuromuscular stimulation device comprising:
  a) a plurality of electrode output cables having a front section and a back section, where the front section has attached a pair of electrodes that are adapted to be attached to selectable areas of a living tissue, and
  b) an electronic control unit attached to a power source and having circuit means for selectively producing a plurality of nerve stimulation pulses which are applied to the living tissue through at least two paired-dipole PLUS OUTPUT connectors, into which the back section of said electrode output cables are attached wherein said electronic control unit circuit means comprises:
   (1) a power input circuit comprising a battery charger having an input that is applied an a–c power source and an output that is applied to a charge/run switch having a CHARGE contact and a RUN contact, where when said switch is placed in its CHARGE position, a rechargeable battery is maintained in a charged condition,
   (2) a power application circuit comprising:
     (a) a latching relay having a normally-open first contact a first coil and a second coil, and
     (b) a normally open START switch that when closed, and the charge/run switch is in the RUN position, said relay is energized allowing the battery voltage to be applied to the input terminal of a voltage regulator and to a POWER ON indicator lamp,
   (3) a power control circuit comprising a power control unit that is energized by a low voltage detector that senses when the battery voltage has dropped to an unacceptable operating level, at which time a LOW BATTERY indicating lamp illuminates, and by a treatment concluded output signal applied when a patient's treatment has been concluded, when said power unit is energized, it produces an output that de-energizes said latching relay that terminates the power to said device.
   (4) a PULSE PATTERN SELECT switch that produces an output signal corresponding to a specific pulse output pattern,
   (5) a pulse-pattern generating circuit comprising a microprocessor that functions in combination with a programmable read only memory (PROM) and a firmware program, where said pulse-pattern generating circuit has a first input that is applied the energizing voltage from said voltage regulator, a second input from said PULSE-PATTERN SELECT switch that selects the specific pulse pattern that is to be processed, a plurality of pulse outputs, and a treatment concluded output signal that automatically de-energizes said power control unit when a patient's treatment time has been concluded,
   (6) a pulse driving circuit comprising a plurality of FET drivers that are applied the respective plurality of output signals from said pulse-pattern generating circuit and that produce a corresponding set of first and second output signals, where the second output signals are applied to an ORing circuit that when enabled, energizes a STIMULUS ON indicating lamp, and
   (7) a pulse output circuit comprising a plurality of isolation and impedance matching transformers and a plurality of POWER SET switch/potentiometer units where the output signals from said pulse driving circuit are applied to a respective transformer and to the pole of the switch, where when the potentiometer is adjusted so that the switch is closed, the selected nerve stimulation pulse is routed through the potentiometer wiper and said coupling capacitor to the paired-dipole PULSE OUTPUT connector to where said electrode output cable attaches.

2. The device as specified in claim 1 wherein said device incorporates four output channels comprising channel 1 through 4, where channels 1 and 3 are timed together, and channels 2 and 4 are timed together.

3. The device as specified in claim 1 wherein said device incorporates six output channels comprising channels 1 through 6, where channels 1, 3 and 5 are timed together and channels 2, 4 and 6 are timed together.

4. The device as specified in claim 1 wherein said rechargeable battery is comprised of a nickel-cadmium battery.

5. The device as specified in claim 1 wherein said pattern selector switch is comprised of a binary encoded switch.

6. The device as specified in claim 1 wherein said programmable read only memory is comprised of a replaceable electronic programmable read only memory (EPROM) having means for allowing said firmware program to be altered or changed to accommodate the parameters of a specific nerve stimulation pulse(s).

7. The device as specified in claim 1 wherein said programmable read only memory is comprised of a replaceable electronic programmable read only memory (EPROM) having means for allowing said firmware program to be altered or changed to accommodate the parameters of a specific nerve stimulation pulse(s), wherein said PROM or EPROM is programmed to provide the following nerve stimulation pulse parameters:

a) pulse width, b) pulse train duration, c) pulse train delay/overlap, d) pulse train ramp (ramp frequency), e) pulse train frequency, f) pulse train repetition cycling, and g) pulse train on-time.

8. The device as specified in claim 1 wherein said nerve stimulation pulses are comprised of individual pulses that are arranged into pulse trains and a pulse train patterns.

9. The device as specified in claim 1 wherein said nerve stimulation pulses are comprised of individual pulses that are arranged into pulse trains and a pulse train patterns, wherein said individual pulses are comprised of either a monophasic square wave or a biphasic asymmetric square wave, where the monophasic square wave has an amplitude that ranges between 0 and 150 volts and a pulse duration that ranges between 40 and 50 microseconds; and the biphasic asymmetric square wave has an amplitude that ranges between 0–150 volts and a positive-phase pulse duration that ranges between 40 and 50 microseconds.

10. The device as specified in claim 1 wherein said nerve stimulation pulses are comprised of individual pulses that are arranged into pulse trains and a pulse train patterns, wherein said individual pulses are comprised of either a monophasic square wave or a biphasic symmetric square wave, where the monophasic square wave has an amplitude that ranges between 0 and 150 volts and a pulse duration that ranges between 40 and 50 microseconds; and the biphasic asymmetric square wave has an amplitude that ranges between 0–150 volts and a positive-phase pulse duration that ranges between 40 and 50 microseconds, and where said pulse trains operate at a pulse rate interval of between 10 and 30 milliseconds which corresponds to a frequency of between 50 Hz and 100 Hz respectively.

11. The device as specified in claim 1 wherein said nerve stimulation pulses are comprised of individual pulses that are arranged into pulse trains and a pulse train patterns, wherein said individual pulses are comprised of either a monophasic square wave or a biphasic asymmetric square wave, where the monophasic square wave has an amplitude that ranges between 0 and 150 volts and a pulse duration that ranges between 40 and 50 microseconds; and the biphasic asymmetric square wave has an amplitude that ranges between 0–150 volts and a positive-phase pulse duration that ranges between 40 and 50 microseconds, and where said pulse trains operate at a pulse rate interval of between 10 and 30 milliseconds which corresponds to a frequency of between 50 Hz and 100 Hz respectively, and wherein said pulse train pattern is comprised of a sequential pulse train pattern that utilizes output channels 1 and 2 to produce two pulse train patterns, a first pulse train pattern on channel 1 and a second pulse train pattern on channel 2, where the second pulse train pattern commences after the first pulse train pattern has ended.

12. The device as specified in claim 1 wherein said nerve stimulation pulses are comprised of individual pulses that are arranged into pulse trains and a pulse train patterns, wherein said individual pulses are comprised of either a monophasic square wave or a biphasic asymmetric square wave, where the monophasic square wave has an amplitude that ranges between 0 and 150 volts and a pulse duration that ranges between 40 and 50 microseconds; and the biphasic asymmetric square wave has an amplitude that ranges between 0–150 volts and a positive-phase pulse duration that ranges between 40 and 50 microseconds, and where said pulse trains operate at a pulse rate interval of between 10 and 30 milliseconds which corresponds to a frequency of between 50 Hz and 100 Hz respectively, and said pulse train pattern is comprised of a sequential pulse train pattern that utilizes output channels 1 and 2 to produce two pulse train patterns, a first pulse train pattern on channel 1 and a second pulse train pattern on channel 2, where the second pulse train pattern commences after the first pulse train pattern has ended, and wherein a typical sequential pulse train pattern is comprised of a first pulse train pattern that lasts for 200 milliseconds, at the conclusion of the first pulse train pattern there is a time delay of between 60–200 milliseconds, typically 160 milliseconds, before the second pulse train pattern of 200 milliseconds commences.

13. The device as specified in claim 1 wherein said nerve stimulation pulses are comprised of individual pulses that are arranged into pulse trains and a pulse train patterns, wherein said individual pulses are comprised of either a monophasic square wave or a biphasic asymmetric square wave, where the monophasic square wave has an amplitude that ranges between 0 and 150 volts and a pulse duration that ranges between 40 and 50 microseconds; and the biphasic asymmetric square wave has an amplitude that ranges between 0–150 volts and a positive-phase pulse duration that ranges between 40 and 50 microseconds, and where said pulse trains operate at a pulse rate interval of between 10 and 30 milliseconds which corresponds to a frequency of between 50 Hz and 100 Hz respectively, and said pulse train pattern is comprised of a delayed, overlapping pulse-train pattern that utilizes output channels 1 and 2 to produce two pulse train pattern: a first pulse train pattern on channel 1 and a second pulse train pattern on channel 2, that commences at a specified time period prior to the termination of the first pulse train pattern on channel 1.

14. The device as specified in claim 1 wherein said nerve stimulation pulses are comprised of individual pulses that are arranged into pulse trains and a pulse train patterns, wherein said individual pulses are comprised of either a monophasic square wave or a biphasic asymmetric square wave, where the monophasic square wave has an amplitude that ranges between 0 and 150 volts and a pulse duration that ranges between 40 and 50 microseconds; and the biphasic asymmetric square wave has an amplitude that ranges between 0–150 volts and a positive-phase pulse duration that ranges between 40 and 50 microseconds, and where said pulse trains operate at a pulse rate interval of between 10 and 30 milliseconds which corresponds to a frequency of between 50 Hz and 100 Hz respectively, and said pulse train pattern is comprised of a delayed, overlapping pulse-train pattern that utilizes output channels 1 and 2 to produce two pulse train pattern; a first pulse train pattern on channel 1 and a second pulse train pattern on channel 2, that commences at a specified time period prior to the termination of the first pulse train pattern on channel 1 where a typical delayed, overlapping pulse-train pattern is comprised of a first pulse train pattern has reached a time period of between 140 and 190 milliseconds, typically 160 milliseconds, the second pulse train pattern of 200 milliseconds commences.

15. The device as specified in claim 1 wherein said nerve stimulation pulses are comprised of individual pulses that are arranged into pulse trains and a pulse train patterns, wherein said individual pulses are comprised of either a monophasic square wave or a biphasic asymmetric square wave, where the monophasic square wave has an amplitude that ranges between 0 and 150 volts and a pulse duration that ranges between 40 and 50 microseconds; and the biphasic asymmetric square wave has an amplitude that ranges between 0–150 volts and a positive-phase pulse duration that ranges between 40 and 50 microseconds, and where said pulse trains operate at a pulse rate interval of between 10 and 30 milliseconds which corresponds to a frequency of between 50 Hz and 100 Hz respectively, wherein said pulse train pattern is comprised of a triple-phase overlapping pulse-train pattern that utilizes channels 1 and 3 to produce three pulse train patters: a first pulse train pattern on channel 1, a second pulse train pattern on channel 2 and a third pulse train pattern on channel 1, where the second pulse train pattern commences at a specified time period prior to the termination of the first pulse train pattern, then after a specified time period and prior to the termination of the second pulse train pattern, the third pulse train pattern, which has a shorter time duration than that of the first pulse train pattern commences.

16. The device as specified in claim 1 wherein said nerve stimulation pulses are comprised of individual pulses that are arranged into pulse trains and a pulse train patterns, wherein said individual pulses are comprised of either a monophasic square wave or a biphasic asymmetric square wave, where the monophasic square wave has an amplitude that ranges between 0 and 150 volts and a pulse duration that ranges between 40 and 50 microseconds; and the biphasic asymmetric square wave has an amplitude that ranges between 0–150 volts and a positive-phase pulse duration that ranges between 40 and 50 microseconds, and where said pulse trains operate at a pulse rate interval of between 10 and 30 milliseconds which corresponds to a frequency of between 50 Hz and 100 Hz respectively, wherein said pulse train pattern is comprised of a triple-phase overlapping pulse-train pattern that utilizes channels 1 and 3 to produce three pulse train patterns; a first pulse train pattern on channel 1, a second pulse train pattern on channel 2 and a third pulse train pattern on channel 1, where the second pulse train pattern commences at a specified time period prior to the termination of the first pulse train pattern, then after a specified time period and prior to the termination of the second pulse train pattern, the third pulse train pattern, which has a shorter time duration than that of the first pulse train pattern commences, and wherein a typical triple-phase overlapping pulse-train pattern is comprised of a first pulse train pattern that lasts for 200 milliseconds, when this pulse train pattern has reached a timer period of between 150 and 170 milliseconds, typically 160 milliseconds, the second pulse train pattern of 200 milliseconds commences which provides a first overlap of 40 milliseconds, when the second pulse train pattern has reached a time period of between 170 and 190 milliseconds, typically 180 milliseconds, the third pulse train pattern which has a time period of 100 milliseconds commences prior to the termination of the second pulse train pattern to provide a second overlap of 20 milliseconds and a time lapse of 120 milliseconds between the termination of the first pulse train pattern and the beginning of the third pulse train pattern.

17. The device of specified in claim 1 wherein said nerve stimulation pulses are comprised of individual pulses that are arranged into pulse trains and a pulse train patterns, wherein said individual pulses are comprised of either a monophasic square wave or a biphasic asymmetric square wave, where the monophasic square wave has an amplitude that ranges between 0 and 150 volts and a pulse duration that ranges between 40 and 50 microseconds; and the biphasic asymmetric square wave has an amplitude that ranges between 0–150 volts and a positive-phase pulse duration that ranges between 40 and 50 microseconds, and where said pulse trains operate at a pulse rate interval of between 10 and 30 milliseconds which corresponds to a frequency of between 50 Hz and 100 Hz respectively, and wherein said pulse train pattern is comprised of a reciprocal pulse train having a second pulse train pattern on channel 2 that commences before the termination of first pulse train pattern on channel when the second pulse train pattern commences with an overlapping ramp that begins at a low voltage amplitude and ramps up to the maximum voltage amplitude that is available at the termination of the first pulse train pattern.

18. The device as specified in claim 1 wherein said nerve stimulation pulses are comprised of individual pulses that are arranged into pulse trains and a pulse train patterns, wherein said individual pulses are comprised of either a monophasic square wave or a biphasic asymmetric square wave, where the monophasic square wave has an amplitude that ranges between 0 and 150 volts and a pulse duration that ranges between 40 and 50 microseconds; and the biphasic asymmetric square wave has an amplitude that ranges between 0–150 volts and a positive-phase pulse duration that ranges between 40 and 50 microseconds, and where said pulse trains operate at a pulse rate interval of between 10 and 30 milliseconds which corresponds to a frequency of between 50 Hz and 100 Hz respectively, and wherein said pulse train pattern is comprised of a delayed sequenced "spring interval" pulse train on channel 1 that switches from one pulse train rate and pulse train duration to another pulse train pattern having a different pulse train rate and pulse train duration, concurrently with the pulse train pattern on channel 1 there is on channel 2, similar but staggered pulse train patterns.

19. An electronic neuromuscular stimulation device comprising:

a) a plurality of electrode output cables with each cable having a front section that splits into a first end and a second end with each end having respectively attached a positive transcutaneous electrode pad and a negative transcutaneous electrode pad, where the pads are adapted to be attached to selectable areas of a human body and where the back section has attached at male jack, b) a utility power cable having on a first end an a–c male connector that plugs into a 120-volt a–c utility power receptacle and on a second end a female connector, and c) an electronic control unit housed within an enclosure having a male power input receptacle that receives the female connector on said utility power cable, a plurality of PULSE OUTPUT connectors that internally interface with output channels where each connector externally interfaces with a respective male jack on one of said plurality of electrode output cables, said electronic control unit having circuit means for selectively producing a plurality of nerve stimulation pulse train patterns which are applied to the patient through the PULSE OUTPUT connectors and said plurality of electrode pads on said electrode output cables, wherein said electronic control unit circuit means comprises:

(1) a power input circuit that is applied 120-volt a–c when the female connector on said utility power cable is inserted into a male-power input receptacle on said enclosure, where said a–c power input is conditioned by and applied through a battery charger that is connected to a CHARGE contact of a single-pole double-throw charge/run switch also having a RUN contact and a pole, where the pole is connected to the positive terminal of a rechargeable battery that has its negative terminal connected to circuit ground, (2) a power application circuit comprising:
 (a) a latching relay having a pole, a normally-open first contact, a second contact, a first coil having a first end and a second end, and a second coil having a first end and a second end, where the relay pole and the first end of the first coil are connected to the RUN contact of the charge/run switch and the first end of the second coil is connected to a first junction to which is also connected the second contact of the relay
 (b) a normally open push-button START switch having a first contact connected to the second end of the first coil and a second contact connected to circuit ground,
 (c) a POWER-ON indicator lamp having a first terminal connected to the first junction and a second terminal connected to circuit ground, and
 (d) a voltage regulator having an input terminal and an output terminal where the input is connected to the first junction, and (3) a power control circuit comprising:
 (a) a power control unit having an output terminal, a first input terminal and a second input terminal, where the output terminal is connected to the second end of the second coil, and
 (b) a low-voltage detector having an input terminal that is connected to the first junction, a first output terminal that is connected to the first input terminal of said power control unit and a second output terminal that is connected to a LOW-BATTERY indicating lamp, (4) a PULSE-PATTERN SELECT switch having means for providing logic level signals that function to select a plurality of output pulse trains and train patterns, (5) a pulse pattern generating circuit that includes a microprocessor that functions in combination with a programmable read only memory (PROM) and a firmware program, with said pulse pattern generating circuit having:
 (a) a first input supplied from the output of said voltage regulator, that energizes said pulse pattern generating circuit,
 (b) a second input supplied from said pulse-pattern selector switch that allows the selection of the specific pulse train and train pattern that is to be processed by said pulse pattern generating circuit,
 (c) a plurality of pulse outputs, and
 (d) a treatment concluded output signal that is automatically applied to said power control unit to turn said device off when a patient's treatment has been concluded, (6) a pulse driving circuit comprising:
 (a) a plurality of FET drivers having input terminals that are applied the respective output signals from said pulse-pattern generating circuit, with each said FET driver having a first output terminal and a second output terminal, and
 (b) an ORing circuit having a plurality of input terminals that are applied the first inputs from said FET drivers, with said ORing circuit having an output terminal that is connected to a STIMULUS ON indicating lamp, and (7) a pulse output circuit comprising:
 (a) a plurality of isolation and impedance matching transformers where each said transformer has a primary winding having a first terminal and a second terminal, and an isolated secondary winding having a first terminal and a second terminal,
 (b) a plurality of PULSE SET switch/potentiometer units, where each switch consists of a single-pole single-throw switch having a pole and a contact, where the contact of each switch is connected to a second junction to which is also connected the third input of said microprocessor, and where each potentiometer has a wiper, a first terminal and a second terminal, where the first terminal of the transformer's primary winding is connected to the battery voltage $V_B$ and to the pole of each switch, and the second terminal of the primary winding is connected to the output of a respective FET driver, and where the first terminal and second terminal of the secondary winding is connected respectively across the first and second terminals of the potentiometer, with the wiper of each potentiometer is capacitively coupled through a capacitor to a positive contact of a respective PULSE OUTPUT connector on said enclosure, where said electronic control circuit operates said electronic neuromuscular device as follows: the input power into said electronic control unit is applied from said utility power cable through said battery charger to said charge/run switch, and when said charge/run switch is placed in the CHARGE position, the rechargeable battery is charged through the pole of said switch, where when said switch is placed in the RUN position, the battery voltage is applied to the pole of said latching relay which is normally in contact with the normally open contact of said relay, when said push-button START switch is depressed, the battery voltage energizes said relay causing the relay pole to make contact with the second contact of said relay, at this occurrence, the battery voltage is applied to a first junction to which is also connected the input terminal of said 5-volt voltage regulator and the POWER-ON indicator lamp, where the power-on mode of said relay is controlled by said relay's second coil which is connected to the output terminal of said power control unit, when the low voltage detector senses that the voltage level of said battery voltage has dropped to a level of 8.5 volts, it energizes the LOW-BATTERY indicating lamp, when the battery voltage drops to an unacceptable level of 7.5 volts, the detector energizes said power control unit which then de-energizes said relay and causes said device to turn off, the power control unit is also energized to turn said device off when the treatment concluded output signal is applied by said pulse processing circuit when a patient's treatment has been concluded; the power output from said voltage regulator is applied to said pulse-pattern generating circuit where said microprocessor in combination with said PROM and said firmware produces a plurality of output signals as selected by said PULSE-PATTERN SELECT switch, the output signal from said pulse-pattern generating circuit are each applied through the respective FET drivers which have an output that is connected to the respective primary winding of said isolation and impedance matching transformer, to said ORing circuit that when enabled, causes said STIMULUS ON indicating lamp to illuminate, and to the pole of the switch on said PULSE SET switch/potentiometer unit; the secondary winding of said transformer is connected across the respective potentiometer of said PULSE SET switch/potentiometer unit, when the potentiometer is adjusted so that the switch is closed, the selected pulse output can be adjusted and routed through the potentiometer wiper and said coupling capacitor to the PULSE OUTPUT connector that attaches to said electrode output cable from where the nerve stimulation pulse is applied to the patient via said electrode output cable.

* * * * *